United States Patent [19]

Eisenhuth et al.

[11] Patent Number: 4,468,526

[45] Date of Patent: Aug. 28, 1984

[54] PROCESS FOR THE PREPARATION OF THIURAM DISULFIDES

[75] Inventors: Ludwig Eisenhuth, Elsenfeld; Hans G. Zengel, Kleinwallstadt; Manfred Bergfeld, Erlenbach, all of Fed. Rep. of Germany

[73] Assignee: Akzona Incorporated, Asheville, N.C.

[21] Appl. No.: 349,353

[22] Filed: Feb. 16, 1982

[30] Foreign Application Priority Data

Feb. 16, 1981 [DE] Fed. Rep. of Germany ....... 3105587

[51] Int. Cl.$^3$ .......................................... C07C 155/10
[52] U.S. Cl. ..................................... 564/76; 544/160; 546/245; 548/523
[58] Field of Search ........................................ 564/76

[56] References Cited

U.S. PATENT DOCUMENTS

| | | | |
|---|---|---|---|
| 3,116,328 | 12/1963 | Cox et al. | 564/76 |
| 3,116,329 | 12/1963 | Hayes et al. | 564/76 |
| 3,248,400 | 4/1966 | Flieg et al. | 564/76 X |
| 3,737,431 | 6/1973 | Campbell et al. | 564/76 X |
| 3,992,448 | 11/1976 | Parkinson | 564/76 |
| 4,120,764 | 10/1978 | Torii et al. | 564/76 X |
| 4,144,272 | 3/1979 | Bergomi et al. | 564/76 |

OTHER PUBLICATIONS

Issoire et al., CA 55: 1641a (1961).
Rothstein et al., CA 49: 146469 (1955).

*Primary Examiner*—Thomas A. Waltz
*Attorney, Agent, or Firm*—Francis W. Young; Daniel N. Christus; Jack H. Hall

[57] ABSTRACT

A process for the preparation of thiuram disulfides substituted with aliphatic, cycloaliphatic, araliphatic, or aromatic hydrocarbon radicals, said process comprising reacting a suitably substituted secondary amine with carbon disulfide and in the presence of a tertiary amine or ammonia, oxygen or oxygen-containing gas, a solvent, and a metalliferous catalyst, at a temperature of between 0° C. and 200° C.

9 Claims, No Drawings

PROCESS FOR THE PREPARATION OF THIURAM DISULFIDES

BACKGROUND OF THE INVENTION

The invention refers to a process for the preparation of thiuram disulfides substituted with aliphatic, cycloaliphatic, araliphatic and/or aromatic hydrocarbon radicals by reacting a suitably substituted secondary amine with carbon disulfide in the presence of oxygen or a gas containing oxygen, a metalliferous catalyst, and a tertiary amine or ammonia.

Making use of known processes, thiuram disulfides can be obtained by the oxidative dimerization of salts of substituted dithiocarbamic acids. Hydrogen peroxide, nitrogen dioxide, chlorine, bromine, iodine, ozone, oxygen, sodium nitrite, sodium hypochlorite, sulfur chlorides, potassium perbromate, selenic acid, or ammonium persulfate are used as oxidant. Tetramethyl thiuram disulfide, one of the most important representatives of this category of compounds, is made on an industrial scale by means of a two-stage process. In the first stage, dimethylamine and carbon disulfide in aqueous sodium hydroxide are reacted to form sodium-N,N-dimethyl dithiocarbonate. In the second stage the dithiocarbamate is oxidized with hydrogen peroxide in the presence of sulfuric acid (Bios 1150, Fiat 1018), with chlorine (U.S. Pat. Nos. 2,751,514 and 2,751,416), or electrolytically (German patent application disclosure Nos. 28 02 260 and 28 03 591).

In the process of German Pat. No. 12 26 564, a secondary alkyl-, aryl- or alkylarylamine is reacted with carbon disulfide in an aqueous or non-aqueous medium and in the presence of an oxygen-containing gas and a metal catalyst to form substituted thiuram disulfide. A sulfonated or carboxylated metal phthalocyanine of the 8th group of the periodic system, as for example cobalt phthalocyanine, is used as catalyst. In this process, the yield is relatively low; at best, it is about 25% of theoretical. When aromatic amines such as diphenylamine are used, the process of German Pat. No. 12 26 564 does not result in the formation of thiuram disulfide. In addition, the preparation and industrial use of the cobalt catalyst are problematical.

The use of a metalliferous catalyst in the oxidation of alkali salts of substituted dithiocarbamic acids with oxygen is also known. According to the process of German published application No. 11 65 011, the oxidation is carried out in an aqueous solution of a sulfonated or carboxylated Group VIII metal phthalocyanine at a pH of about 7 to 12. However, materials used in this process add to its expense and form unusable byproducts. Lye is needed for the preparation of the dithiocarbamates and hydrochloric acid is required for pH adjustment, and these form unusable sodium chloride. Further, the industrial preparation and application of these Group VIII metalliferous catalysts is problematical.

The use of an ammonium salt of dithiocarbamic acid, instead of the alkali salts, is also already known. In the process of German patent application disclosure No. 25 27 898, ammonium dimethyldithiocarbamate is oxidized by means of hydrogen peroxide in an aqueous solution of sulfuric acid at a pH of from 5 to 7 to yield a suspension of solid tetramethyl thiuram disulfide in an aqueous ammonium sulfate solution. After the solid tetramethyl thiuram disulfide has been filtered off the resulting filtrate must be concentrated down to the solubility limit of the ammonium sulfate, resulting in its precipitation. The ammonium sulfate could be used as a fertilizer, but only if the adhering dithiocarbamate is removed. This makes the ammonium sulfate an undesirable byproduct.

Thus, there is a need for a process for the preparation of a thiuram disulfide substituted with aliphatic, cycloaliphatic, araliphatic and/or aromatic hydrocarbon radicals, by reacting a suitably substituted secondary amine with carbon disulfide in a solvent and in the presence of oxygen or a gas containing oxygen and a metalliferous catalyst. The reaction is carried out at temperatures of from 0° to 200° C., and a preferred embodiment comprises reacting the carbon disulfide and the secondary amine in a molar ratio of 1.0 to 1.2:1 in the presence of a tertiary amine or ammonia, oxygen or a gas containing oxygen, and the metalliferous catalyst. Another embodiment comprises reacting equimolar quantities of carbon disulfide, the secondary amine, and a tertiary amine or ammonia, and thereafter reacting the resulting reaction mixture with carbon disulfide in the presence of the metalliferous catalyst and oxygen or a gas containing oxygen. A still further embodiment comprises reacting carbon disulfide, the secondary amine, and a tertiary amine or ammonia to form the dithiocarbamate, which is subsequently isolated and reacted in the presence of the metalliferous catalyst and oxygen or a gas containing oxygen. The catalyst may be selected from one or more of the group including copper, silver, gold, zinc, cadmium, mercury, lanthanum, cerium, titanium, zirconium, vanadium, nicobium, tantalum, chromium, molybdenum, tungsten, uranium, manganese, rhenium, iron, cobalt, as well as nickel, or derivatives of the mentioned metals.

Suitable aliphatically substituted secondary amines include: dimethylamine, diethylamine, dipropylamine, diisopropylamine, dibutylamine, di-sec-butylamine, di-tert.-butylamine, di-(2-methylpropyl)-amine, dipentylamine, di-(1-methylbutyl)-amine, di-(2-methylbutyl)-amine, di-(3-methylbutyl)-amine, di-(1,1-methylpropyl)-amine, di-(2,2-dimethylpropyl)-amine, di-(1,2-dimethylpropyl)-amine, dihexyl-amine, di-(1-methylpentyl)-amine, di-(2-methylpentyl)-amine, di-(3-methylpentyl)-amine, di-(3-ethylpentyl)-amine, di-(1,1-dimethylbutyl)-amine, di-(2,2-dimethylbutyl)-amine, di-(3,3-dimethylbutyl)-amine, di-(2,3-dimethylbutyl)-amine, di-(1-ethylbutyl)-amine, di-(2-ethylbutyl)-amine, diheptylamine, di-(1-methylhexyl)-amine, di-(2-methylhexyl)-amine, di-(3-methylhexyl)-amine, di-(4-methylhexyl)-amine, di-(5-methylhexyl)-amine, di-(1-ethylpentyl) amine, di-(2-ethylpentyl)-amine, di-(3-ethylpentyl)-amine, dioctylamine, di-(1-methylheptyl)-amine, di-(2-methylheptyl)-amine, di-(3-methylheptyl)-amine, di-(4-methylheptyl)-amine, di-(5-methylheptyl)-amine, di-(6-hexyl)-amine, di-(3-ethylhexyl)-amine, di-(4-ethylhexyl)-amine, methylethylamine, ethylbutylamine, dilaurylamine, didodecylamine, ditridecylamine, dipalmitylamine, distearylamine and dioleylamine.

Suitable aromatically-substituted secondary amines include: diphenylamine, 4,4'-dimethyldiphenylamine, 3,3'-dimethyldiphenyl-amine, 2,2'-dimethyldiphenylamine, as well as alkylarylamines, such as N-methylaniline, N-ethylaniline, N-propylaniline, N-isopropylaniline, N-butylaniline, N-sec.-butylaniline, N-tert.-butylaniline, N-pentylaniline, N-(1-methylbutyl)-aniline, N-(2-methylbutyl)-aniline, N-(3-methylbutyl)-aniline, N-(1,1-dimethylpropyl)-aniline, N-(2,2-dimethylpropyl)-aniline, N-(1,2-dimethylpropyl)-aniline, N-(1- methylpropyl)-aniline, N-(2-methylpentyl)-aniline, N-(3-methylpentyl)-aniline, N-(4-methylpentyl)-aniline, N-(1,1-dimethylbutyl)-aniline, N-(2,2-dimethylbutyl)-aniline, N-(3,3-dimethylbutyl)-aniline, N-(2,3-dimethylbutyl)-aniline, N-(1-ethylbutyl)-aniline, N-(2-ethylbutyl)-aniline, N-heptylaniline, N-(1-methylhexyl)-aniline, N-(2-methylhexyl)-aniline, N-(3-methylhexyl)-aniline, N-(1-ethylpentyl)-aniline, N-(2-ethylpentyl)-aniline, N-(3-ethylpentyl)-aniline, N-octyl-aniline, N-(1-methylpentyl)-aniline, N-(2-methylheptyl)-aniline, N-(4-methylheptyl)-aniline, N-(4-methylpentyl)-aniline, N-(5-methylheptyl)-aniline, N-(6-methylheptyl)-aniline, N-(1-ethylhexyl)-aniline, N-(2-ethylhexyl)-aniline, N-(3-ethylhexyl)-aniline, N-(3-ethylhexyl)-aniline, as well as the corresponding alkyl-naphthylamines.

Suitable araliphatic secondary amines are the listed aliphatic and cycloaliphatic amines, in which one or several hydrogen atoms located on the hydrocarbon radicals are substituted by aryl radicals, as for example the following: dibenzylamine, di-(phenylethyl)-amine, di(2-phenylpropyl)-amine, di-(3-phenylpropyl)-amine, N-methylbenzylamine, N-ethylbenzyl-amine, N-propylbenzylzmine.

Examples of suitable cycloaliphatically-substituted secondary amines are the compounds hydrated in the nucleus corresponding to the above-mentioned aromatically-substituted secondary amines, as well as corresponding amines with cyclobutyl, cyclopentyl, cycloheptyl, or cyclooctyl substituents. As already stated above, the substituents of the secondary amine may be identical or different. They may, however, also be concyclic amines such as morpholine, piperidine, pyrrolidine and their derivatives.

Suitable tertiary amines are selected from the aliphatic, cycloaliphatic, aromatic and heterocylic amines, such as trimethylamine, triethylamine, tri-n-propylamine, tri-n-butylamine, n-octyl-dimethylamine, di-isopropyl-ethylamine, propyldimethylamine, ethyl-dimethylamine, isopropyl-dimethylamine, butyl-dimethylamine, N-methylpyrrolidine, N-dimethylaminopyridine and 1,4-diazobicyclo-(2,2,2)-octane.

In the process pursuant to the invention, the oxidant used is oxygen or a gas containing oxygen, such as air. Non-aqueous solvents suitable for use in the process pursuant to the invention include aromatic hydrocarbons such as benzene, toluene, xylene, nitrobenzene; aliphatic esters; alkylether; lower alcohols, such as methanol, ethanol, isopropanol, n-propanol, n-butanol, t-butanol and amyl alcohol; chlorinated hydrocarbons, such as dichloromethane, chloroform, dichloroethane, trichloroethane; and aprotic solvents, such as dimethyl formamide, acetonitrile, dimethylacetamide, dimethyl sulfoxide and hexamethyl phosphoric triamide. Suitable aqueous solvents include water/alcohol mixtures. High yields and selectivities may be obtained in pure water, but in general the reaction rate in water is slower than in the above-mentioned non-aqueous solvents. Preferred solvents include aromatic hydrocarbons, low alcohols and alcohol/water mixtures.

The process pursuant to the invention is carried out at temperatures in the range from 0° to 200° C., preferably from 20° to 90° C. Temperatures below 90° C. are preferred for reasons of economic and safety. Preferred oxygen pressures or partial oxygen pressures are those no less than 0.1 bar. As is to be expected, the reaction rate increases with rising oxygen pressures.

The metals listed in the patent claims, or their derivatives, are used as metalliferous catalysts. In addition to the claimed catalysts, all other metals of the sub-groups of the periodic system of elements and their derivatives are suitable, but are not preferred for reasons of cost. Excellent metalliferous catalysts include cerium, manganese, copper, iron, cobalt, molybdenum or vanadium in elemental form, as salts, oxides, or complexes, or in the form of their organic compounds. Among the preferred metals or their derivatives, copper, manganese and cerium are more catalytically effective than iron, cobalt, molybdenum and vanadium.

Elementary copper is preferably used in the form of copper powder. Copper compounds to be considered are all mono- or divalent inorganic, organic, simple, or complex copper salts. Examples of suitable monovalent copper salts are copper(I) chloride, bromide and iodide, addition compounds of these copper(I) halides with carbon monoxide, complex copper(I) salts, such as the alkali chlorocuprates, complex ammoniacates of copper(I) cyanide, such as cyanocuprates, e.g. potassium tricyanocuprate(I), double salts with copper(I) thiocyanate, copper(I) acetate, copper(I) sulfide and complex double sulfides of copper(I) sulfide and alkali polysulfides. Examples of suitable copper(II) salts are copper(II) chloride, bromide, sulfide, nitrite, thiocyanate, or cyanide, Cu(II) salts of carboxylic acids, such as copper(II) acetate, copper dithiocarbamate, as well as the complex ammoniacates of copper(II) salts. Copper(I) oxide is also very well suited as catalyst.

Suitable manganese-containing catalysts include powdered manganese, manganese dioxide, potassium permanganates, manganese acetate, manganese dithiocarbamates, and the manganese derivatives corresponding to the above-mentioned copper compounds. Suitable cerium catalysts include metallic cerium, cerium dioxide, cerium(III) chloride, cerium chloride, cerium chlorocomplex salts, cerium nitrate, cerium nitrato salts, cerium sulfate, cerium carbonate, cerium oxalate and the cerium sulfides.

Examples of iron catalysts are the known iron oxides, iron(II) and iron(III) salts, and complex iron salts. Suitable vanadium catalysts include the vanadium oxides, chlorides and sulfates, and the known double and complex salts. Suitable cobalt catalysts are the known cobalt oxides, cobalt (II) salts, and the complex salts.

Finally, the suitable molybdenum catalysts include molybdenium oxides, chlorides, sulfides and fluorides, the molybdates, and the known complex acido salts. Mixtures of several of the above-mentioned catalysts may also be used.

The required quantity of metalliferous catalyst is surprisingly small. Preferably, it is within a range from 0.01 to 5 millimoles per mole of secondary amine. Smaller catalyst quantities can also be used, but the reaction rate is thereby slowed. Larger quantities of catalysts should be avoided, because there is a danger that such larger quantities could precipitate and contaminate the reaction product.

In principle, the process according to the present invention may be carried out according to three procedures. In the first procedure, equimolar quantities of the secondary amine and carbon disulfide are reacted with oxygen in the presence of the metalliferous catalyst and the tertiary amine or ammonia to form thiuram disulfide. The quantity of tertiary amine can be varied within wide limits, from catalytic to stoichiometric quantities. The tertiary amine may also function as a solvent, in which case it may be used in quantities corresponding to or even exceeding the quantity of solvent normally used. In the second procedure, equimolar quantities of carbon disulfide, secondary amine, and the tertiary amine or ammonia are reacted to form a mixture of intermediate products consisting essentially of the corresponding quaternary ammonium salt or ammonium salt of dithiocarbamic acid. This mixture of reaction products is then reacted with oxygen in the presence of the metalliferous catalyst, and it is thereby not necessary to separate the intermediate product(s) before they are reacted further. In the third procedure, equimolar quantities of the secondary amine and the tertiary amine or ammonia are dissolved in a suitable solvent, such as water or an alcohol. An equimolar amount of carbon disulfide, if necessary also dissolved, is then added. The reaction proceeds quickly and in most cases ends after a few minutes, thereby forming the quaternary ammonium dithiocarbamate or the ammonium dithiocarbamate. The solvent quantity is selected in an amount sufficient to ensure that the salt will precipitate as completely as possible so as to facilitate its filtration. In the final reaction step, the dithiocarbamate is reacted with oxygen in the presence of the metalliferous catalyst to form the thiuram disulfide. In the case of the first two procedures, the carbon disulfide is used in at least stoichiometric quantities. Using a 1 to 20 mole percent excess of carbon disulfide increases the thiuram disulfide yield and the reaction selectivity.

The reaction time depends upon the processing conditions and may range from a few minutes to three hours under the preferred temperature and oxygen pressure conditions. The present process comprises forcing oxygen or the gas containing oxygen onto the reaction solution at the given pressure and temperature conditions, or by conducting it into or through the reaction solution. Depending upon the procedure selected, the reaction mixture will consist of solvent, carbon disulfide, secondary amine, tertiary amine or ammonia, and metalliferous catalyst; or of solvent, metalliferous catalyst and quaternary ammonium dithiocarbamate; or of the reaction mixture obtained by reacting secondary amine, tertiary amine or ammonia, and carbon disulfide in a solvent, and a metalliferous catalyst. In most cases, as with tetramethyl thiuram disulfide, the end product precipitates immediately from the reaction mixture and can be filtered off. In other cases, the desired end product is obtained when the reaction mixture is cooled or concentrated. Liquid products are obtained in pure form by distillation or extraction.

In an industrial-scale process pursuant to the invention it is advantageous to circulate the mother liquor so as to obviate the need for constant catalyst replenishment. For example, it is possible to run more than ten high yielding reaction cycles without any loss of catalyst activity. Practically quantitative yields and selectivities of more than 99% can be obtained with the present process. The products obtained have a high degree of purity and can, as a rule, be used as intended without purification.

Compared to the known two-stage process in which the dithiocarbamate is synthesized first, the single-stage process is economical and environmentally less dangerous, since no auxiliary materials are consumed and no by-products are formed. Compared with the single-stage process of German Pat. No. 12 26 564, the present process uses very simple and inexpensive catalysts. Further, soluble catalysts are used in the industrial execution of the process pursuant to the invention, and the catalysts can be circulated several times with the mother liquor without loss of activity, resulting in practically quantitative yields. The thiuram disulfides made pursuant to the invention are used as vulcanization accelerators for synthetic and natural rubber and as agricultural chemicals.

The following examples are illustrative of the present invention:

EXAMPLE 1

This example illustrates the first of the three procedures cited hereinabove. 13.5 g (0.3 mol) of dimethylamine, 15.15 g (0.15 mol) of triethylamine and 24.4 mg ($0.1 \times 10^{-3}$ mol) of manganese(II) acetate. $4H_2O$ in 100 g of isopropanol were dissolved in a 500 ml glass autoclave equipped with a jacket for the circulation of a heating liquid, a thermometer, a pressure measuring device and a stirring device. 25.1 g (0.33 mol) of carbon disulfide were added to this solution. The resulting clear, dark brown solution was heated to 50° C., and oxygen was added at a pressure of 1.7 bar and with vigorous stirring. Oxygen was immediately consumed and the solution became turbid due to the separation of tetramethyl thiuram disulfide.

When absorption of oxygen ended after 95 minutes upon the complete reaction of the dimethyl-amine, the reaction solution changed from a dark brown to a pale yellow color. The white, crystalline precipitate was filtered off, washed with isopropanol, and dried. 35.6 g of a product was obtained. Upon analysis, (elementary analysis, IR, $^1H$-NMR, MS) the product was found to correspond to tetramethyl thiuram disulfide at a chromatographically determined purity of 100% (FP=156° C.). The mother liquor contained another 0.25 g of tetramethyl thiuram disulfide and the originally used, unchanged triethylamine. The total yield of tetramethyl thiuram disulfide therefore was 35.85 g, corresponding to 99.6% of theoretical.

EXAMPLE 2

This example illustrates the second of the three procedures cited hereinabove. A solution of 13.5 g (0.3 mol) of dimethylamine in 100 g of isopropanol was, while being cooled, reacted with 23.6 g (0.31 mol) of carbon disulfide and 30.3 g (0.3 mol) of triethylamine in a glass reaction vessel equipped with reflux cooler and stirring device. Subsequently, the solution obtained in this exothermic reaction was transferred to a 500 ml glass autoclave, mixed with 24.4 mg ($0.1 \times 10^{-3}$ mol) of manganese(II) acetate . $4H_2O$, heated to 50° C. and stirred vigorously, and oxygen was simultaneously applied at a pressure of 1.7 bar. An immediate and rapid absorption of oxygen was observed, and the solution became turbid due to the separation of tetramethyl thiuram disulfide. The reaction had ended after 155 minutes; no more oxygen was absorbed, and the solution changed from a dark brown to a pale yellow color. The white, crystalline precipitate filtered off, washed, and dried was 35.5 g of tetramethyl thiuram disulfide. The mother liquor contained another 0.34 g of this substance, so that the total yield of tetramethyl thiuram disulfide was 35.84 g, corresponding to 99.6% of theoretical.

EXAMPLE 3

This procedure illustrates the third of the three procedures cited hereinabove. 30.4 g (0.4 mol) of carbon disulfide were added with cooling to a solution of 18.0 g (0.4 mol) of dimethylamine and 44.44 g (0.44 mol) of triethylamine in 100 g of methanol. The white precipitate that formed was filtered off, washed with cold methanol, and dried. It consisted of pure triethylammonium dimethyl dithiocarbamate.

66.0 g (0.3 mol) of this substance were dissolved in 100 g of isopropanol in the reaction equipment described in Example 1, mixed with 24.4 mg ($0.1 \times 10^{-3}$ mol) of Mn(CH$_3$COO)$_2$ . 4H$_2$O, heated to 50° C. and stirred vigorously, while oxygen was applied under a pressure of 1.7 bar. An immediate and rapid absorption of oxygen was observed, and the solution became turbid due to the separation of tetramethyl thiuram sulfide.

contained 0.3 g of TMTD and 0.095 g of dimethylamine in the form of dimethyl dithiocarbamate. Thus the conversion, referred to the dimethylamine, amounted to 99.3% and the total yield of tetramethyl thiuram disulfide was 35.6 grams, corresponding to 98.9% of theoretical.

EXAMPLES 7 to 15

The following are reactions similar to that described in Example 1, but the concentration and type of the tertiary amine are varied. "DMA" is dimethylamine. The results are as follows:

| Example No. | Tertiary Amine | Moles (mol) | Catalyst ($10^{-4}$ mol) | Reaction Time (min) | Reacted DMA (%) | Yield of TMTD (%) |
|---|---|---|---|---|---|---|
| 7 | triethylamine | (0.01) | Cu(CH$_3$COO)$_2$ | 180 | 80.3 | 78.5 |
| 8 | triethylamine | (0.3) | " | 180 | 97.6 | 96.4 |
| 9 | triethylamine | (0.4) | " | 180 | 95.6 | 94.0 |
| 10 | diisopropylethylamine | (0.15) | " | 180 | 99.7 | 99.3 |
| 11 | dimethyloctylamine | (0.15) | " | 180 | 84.0 | 82.4 |
| 12 | N—methylpyrrolidine | (0.15) | " | 180 | 94.9 | 93.5 |
| 13 | trimethylamine | (0.2) | Mn(CH$_3$COO)$_2$ | 95 | 100 | 99.4 |
| 14 | tri-n-butylamine | (0.15) | " | 105 | 100 | 97.6 |
| 15 | 1,4-diazobicyclo-(2,2,2)-octane | (0.3) | " | 120 | 100 | 95.7 |

The reaction had ended after 160 minutes, the absorption of oxygen ceasing and the color of the solution changing from dark brown to pale yellow. The fine white crystalline precipitate filtered off, washed, and dried was 35.6 g of tetramethyl thiuram disulfide. The mother liquor contained another 0.3 g of this substance, so that the total yield of tetramethyl thiuram disulfide was 35.9 g, corresponding to 99.7% of theoretical.

EXAMPLES 4 and 5

In a reaction similar to that set forth in Example 1, 13.5 g (0.3 mol) of dimethylamine and 25.1 g (0.33 mol) of carbon disulfide in 100 g of isopropanol were reacted with oxygen (1.7 bar) at 50° C. in the presence of 15.15 g (0.15 mol) of triethylamine and catalytic quantities of manganese(II) acetate. The results obtained with different manganese(II) acetate concentrations are compiled in the following table:

| Example No. | Mn(CH$_3$COO)$_2$ ($10^{-3}$ mol) | Reaction time (min.) | Reacted DMA (%) | Yield of TMTD (%) |
|---|---|---|---|---|
| 4 | 0.5 | 30 | 100 | 99.7 |
| 5 | 0.02 | 450 | 100 | 99.5 |

These examples demonstrate that the catalyst concentration can be varied over a wide range.

EXAMPLE 6

In the reaction equipment described in Example 1, 13.5 g (0.3 mol) of dimethylamine, 7.6 g (0.075 mol) of triethylamine and 20 mg ($0.1 \times 10^{-3}$ mol) of copper(II) acetate. H$_2$O were dissolved in 100 g of isopropanol. 25.1 g (0.33 mol) of carbon disulfide were added thereto, the clear reaction solution was brought to 50° C., and oxygen added at a pressure of 1.7 bar. Oxygen was immediately consumed, and the solution became turbid after a few minutes due to the separation of tetramethyl thiuram disulfide (TMTD). After three hours, with only a small amount of oxygen still being absorbed, the reaction was terminated, and the white crystalline precipitate separated and dried. 35.3 g of pure TMTD were obtained in this manner. The mother liquor still

EXAMPLES 16 to 20

In the following reactions, analogous to that set forth in Example 6, different copper compounds were used as catalysts. 13.5 g (0.3 mol) of dimethylamine and 15.15 g (0.15 mol) of triethylamine in 100 g of isopropanol were used, to which 25.1 g (0.33 mol) of carbon disulfide were added, and this solution was then oxidized for 3 hours at 50° C., with an oxygen pressure of 1.7 bar, in the presence of different copper catalysts.

The results are listed in the following table:

| Example No. | Catalyst | Moles ($10^{-3}$ mol) | Reacted DMA (%) | Yield of TMTD (%) |
|---|---|---|---|---|
| 16 | ((CH$_3$)$_2$NCS$_2$)$_2$Cu | (0.1) | 100 | 99.4 |
| 17 | Cu powder | (0.1) | 83.2 | 81.4 |
| 18 | Cu(SO$_4$)$_2$ | (0.1) | 92.8 | 91.3 |
| 19 | Cu$_2$O | (0.1) | 91.0 | 90.2 |
| 20 | Cu oleate | (0.1) | 99.2 | 98.5 |

EXAMPLES 21 to 26

In the following examples utilizing the procedure of Example 6, different solvents or solvent mixtures were used. 13.5 g (0.3 mol) of dimethylamine, 15.15 g (0.15 mol) of triethylamine, and $0.1 \times 10^{-3}$ mol of copper(II) acetate in the various solvents were added to 21.1 g (0.33 mol) of carbon disulfide. The solution was oxidized for three hours at 50° C. under an oxygen pressure of 1.7 bar. The results are as follows:

| Example No. | Solvent Alcohol | gram | Water (g) | Reacted DMA (%) | Yield of TMTD (%) |
|---|---|---|---|---|---|
| 21 | methanol | 100 | — | 99.2 | 98.2 |
| 22 | ethanol | 100 | — | 98.7 | 98.0 |
| 23 | glycol | 100 | — | 92.5 | 90.1 |
| 24 | toluene | 100 | — | 99.6 | 98.6 |
| 25 | isopropanol | 80 | 20 | 98.5 | 97.8 |

-continued

| Example No. | Solvent Alcohol | gram | Water (g) | Reacted DMA (%) | Yield of TMTD (%) |
|---|---|---|---|---|---|
| 26* | — | | 100 | 89.4 | 86.5 |

*Catalyst: $0.1 \times 10^{-3}$ mol $Mn(CH_3COO)_2 \times 4H_2O$

EXAMPLES 27 to 31

In the following examples, utilizing the procedures of Example 6, different heavy metal compounds were used as catalysts. 13.5 g (0.3 mol) of dimethylamine, 15.15 g (0.15 mol) of triethylamine and $0.1 \times 10^{-3}$ mol of a catalyst were dissolved in 100 g of isopropanol. 25.1 g (0.33 mol) of carbon disulfide was added thereto, and the reaction mixture oxidized with oxygen at 50° C. The results obtained with the various catalysts are compiled in the following table:

| Example No. | Catalyst ($0.1 \times 10^{-3}$ mol) | $O_2$ press. (bar) | Reaction Time (hrs) | Reacted DMA (%) | TMTD Yield (%) |
|---|---|---|---|---|---|
| 27 | $FeSO_4$ | 1.7 | 4.0 | 97.6 | 95.2 |
| 28 | $MoO_2(acac)_2$ | 5.0 | 2.0 | 98.1 | 96.5 |
| 29 | $VOSO_4$ | 5.0 | 3.5 | 96.2 | 94.8 |
| 30 | $OsO_4$ | 5.0 | 4.5 | 97.0 | 95.2 |
| 31 | $Co(CH_3COO)_2$ | 5.0 | 8.5 | 86.4 | 84.8 |

EXAMPLES 32 and 33

The reaction temperature was varied in the following examples. 13.5 g (0.3 mol) of dimethylamine and 15.15 g (0.15 mol) of triethylamine, and a metal catalyst were dissolved in 100 g of methanol in the reaction equipment described in Example 1. 23.6 g (0.31 mol) of carbon disulfide were added thereto, and the reaction mixture oxidized under an oxygen pressure of 5 bar. The results obtained at the various reaction temperatures are:

| Example No. | Catalyst ($0.1 \times 10^{-3}$ mol) | Reaction Temp. (°C.) | Reaction Time (min.) | Reacted DMA (%) | Yield of TMTD (%) |
|---|---|---|---|---|---|
| 32 | $Cu(CH_3COO)_2$ | 25 | 150 | 98.4 | 96.9 |
| 33 | $Mn(CH_3COO)_2$ | 90 | 9 | 100 | 98.6 |

EXAMPLES 34 and 35

The following examples demonstrate the correlation between oxygen pressure and reaction time. 13.5 g (0.3 mol) of dimethylamine, 15.15 g (0.15 mol) of triethylamine, and 20 mg ($0.1 \times 10^{-3}$ mol) of $Cu(CH_3COO)_2 \cdot H_2O$ were dissolved in 100 g of isopropanol in the reaction equipment described in Example 1. 23.6 g (0.31 mol) of carbon disulfide were added thereto, and the reaction mixture oxidized with oxygen at 50° C. The results obtained with the different oxygen pressures are:

| Example No. | $O_2$ pressure (bar) | Reaction Time (min) | Reacted DMA (%) | Yield of TMTD (%) |
|---|---|---|---|---|
| 34 | 1 | 240 | 94.0 | 93.2 |
| 35 | 10 | 50 | 99.5 | 98.6 |

EXAMPLE 36

13.5 g (0.3 mol) of dimethylamine, 7.6 g (0.075 mol) of triethylamine, and 217 mg ($0.5 \times 10^{-3}$ mol) of $Ce(NO_3)_3 \cdot 6H_2O$ were dissolved in 100 g of isopropanol, in a glass reaction vessel equipped with a cooler ($-20°$ C.), thermometer and stirring device. 23.6 g (0.31 mol) of carbon disulfide were added thereto, and the solution was heated to 50° C., stirred vigorously, and a weak stream of air conducted thereover. After a short time the solution became turbid due to the separation of tetramethyl thiuram disulfide. The experiment was stopped after 4 hours, and the white precipitate was filtered off, washed, and dried. 32.2 g of tetramethyl thiuram disulfide were obtained, 89.5% of theoretical. This example demonstrates that oxidation can also be carried out with air and at normal pressure.

EXAMPLE 37

21.9 g (0.3 mol) of diethylamine, 7.6 g (0.075 mol) of triethylamine and 24.4 mg ($0.1 \times 10^{-3}$ mol) of $Mn(CH_3COO)_2 \cdot 4H_2O$ were dissolved in 100 g of isopropanol, in the reaction equipment described in Example 1. To this solution was added 23.6 g of carbon disulfide, and the resulting dark brown solution was heated to 50° C. and stirred vigorously. Oxygen at a pressure of 1.7 bar was applied thereto and absorbed at once. The reaction ended after 80 minutes, at which time there was no further absorption of oxygen and the solution changed from a dark brown to a yellow color. A white, crystalline solid precipitated out upon cooling, which was filtered off, washed with isopropanol, and dried. In this manner, 41.7 g of a product were obtained, which according to elementary analysis, IR, $^1$H-NMR, and MS was tetraethyl thiuram disulfide, and which according to chromatographic analysis had a purity of 100% (FP=72° C.). The mother liquor contained another 1.8 g of tetraethyl thiuram disulfide, which was isolated in pure form by concentrating the solution and washing the residue with isopropanol. Thus, the total yield of tetraethyl thiuram disulfide was 43.5 g, corresponding to 98.0% of theoretical.

EXAMPLE 38

The work was performed in a manner similar to that of Example 37, but 5.1 g (0.3 mol) of ammonia was used instead of the triethylamine, and reaction ended after 28 minutes. 40.6 grams of tetraethyl thiuram disulfide precipitated during cooling, and it was separated, washed and dried. The mother liquor contained another 1.8 g of this product, so that the total yield of tetraethyl thiuram disulfide was 42.4 g, corresponding to 95.5% of theoretical.

EXAMPLE 39

The work was performed in a manner similar to that of Example 37, but instead of manganese(II) acetate, 43.4 mg ($0.1 \times 10^{-3}$ mol) of $Ce(NO_3)_3 \cdot 6H_2O$ was used as catalyst and the reaction was carried out under an oxygen pressure of 1.7 bar and at a temperature of 25° C. Oxygen was absorbed at once, and the solution became turbid after a short time due to the separation of tetraethyl thiuram disulfide. The reaction ended after 90 minutes and the total yield of tetraethyl thiuram disulfide was 43.2 g, corresponding to 97.3% of theoretical.

EXAMPLE 40

32.1 g (0.3 mol) of N-methylaniline, 15.15 g (0.15 mol) of triethylamine, and 24.4 mg ($0.1 \times 10^{-3}$ mol) of Mn(CH$_3$COO)$_2$·4H$_2$O were dissolved in 100 g of isopropanol using the reaction equipment described in Example 1. 23.6 g (0.31 mol) of carbon disulfide were added to this solution. The reaction mixture was brought to 50° C., stirred vigorously, and oxygen applied under a pressure of 1.7 bar. Oxygen was absorbed at once, and the solution became turbid due to the separation of the product. The experiment was terminated after 120 minutes, and the white, crystalline precipitate filtered off, washed, and dried. 49.8 g of the product obtained in this manner was determined by elementary analysis, $^1$H-NMR, IR, and MS to correspond to N,N'-dimethyl-N,N'-diphenyl thiuram disulfide. The yield was 91.2% of theoretical, and the product had a freezing point of 198° C.

EXAMPLE 41

56.4 g (0.2 mol) of triethylammonium-N-methyl-N-phenyl dithiocarbamate and 24.4 mg ($0.1 \times 10^{-3}$ mol) of Mn(CH$_3$COO)$_2$·4H$_2$O in 100 g of isopropanol were reacted at 50° C. with oxygen at 1.7 bar in the reaction equipment described in Example 1. During the reaction, the solution became turbid due to the separation of N,N'-dimethyl-N,N'-diphenyl thiuram disulfide. The experiment was discontinued after 150 minutes. Upon filtration, washing, and drying, 32.8 g of thiuram disulfide was obtained, corresponding to 90.2% of theoretical.

EXAMPLE 42

The work was performed as a comparison with Example 40, but without adding triethylamine as an auxiliary base. No absorption of oxygen was noted, and after three hours the initial materials used had not changed.

EXAMPLE 43

26.1 g (0.3 mol) of morpholine, 15.15 g (0.15 mol) of triethylamine and 24.4 mg ($0.1 \times 10^{-3}$ mol) of Mn(CH$_3$COO)$_2$·4H$_2$O in 100 g of isopropanol were placed in the reaction equipment described in Example 1. 23.6 g (0.31 mol) of carbon disulfide were added thereto. The reaction mixture was heated to 50° C., stirred vigorously and oxygen applied under a pressure of 1.7 bar, follwed by the deposit of a white precipitate after a short time. The reaction ended after five hours, and the precipitate was filtered off, washed, and dried. 46.7 g of a product (FP=145° C.) were obtained in this manner which upon analysis corresponded to di-N,N'-oxydiethylene thiuram disulfide. The yield was 96.1%, referred to the charged morpholine.

EXAMPLE 44

The work was carried out as in Example 43, but without the addition of triethylamine. In this case, there was no oxidation.

EXAMPLE 45

In order to prepare tetra-n-propyl thiuram disulfide, 20.2 g (0.2 mol) of di-n-propylamine, 16.0 g (0.21 mol) of carbon disulfide, 20.2 g (0.2 mol) of triethylamine, and 24.4 mg ($0.1 \times 10^{-3}$ mol) of Mn(CH$_3$COO)$_2$·4H$_2$O were reacted in isopropanol in the manner described in Example 1. The reaction temperature was 50° C., the oxygen pressure 1.8 bar, and the duration of the reaction 70 minutes. Concentration and cooling of the reaction solution produced 35.0 g of a white, crystalline product which upon analysis corresponded to tetra-n-propyl thiuram disulfide. The yield was 98.9% of theoretical and the product had an FP of 60° C.

EXAMPLE 46

In order to prepare tetraisopropyl thiuram disulfide, 30.3 g (0.3 mol) of diisopropylamine, 23.6 g (0.31 mol) of carbon disulfide and 5.05 g (0.05 mol) of triethylamine were reacted in 100 g of isopropanol in the presence of 24.4 mg ($0.1 \times 10^{-3}$ mol) of Mn(CH$_3$COO)$_2$·4H$_2$O and with oxygen, in the manner set forth in Example 1. The oxygen pressure was 1.8 bar, the reaction temperature 50° C., and the duration of the reaction was 70 minutes. The white precipitate formed when the reaction solution was cooled consisted of 34.0 g of the desired thiuram disulfide, which was determined by physical and chemical analysis to be tetraisopropyl thiuram disulfide having an F.P. of 112° C. Another 12.8 g of this substance precipitated when the mother liquor was concentrated, so that the total yield of tetraisopropyl thiuram disulfide was 46.8 g, corresponding to 88.6% of theoretical.

EXAMPLE 47

25.85 g (0.2 mol) of di-n-butylamine, 16.0 g (0.21 mol) of carbon disulfide, 20.2 g (0.2 mol) of triethylamine and 24.4 mg ($0.1 \times 10^{-3}$ mol) of Mn(CH$_3$COO)$_2$·4H$_2$O were reacted with oxygen in 100 g of isopropanol and in the manner described in Example 1. The reaction temperature was 50° C., the oxygen pressure 1.8 bar, and the reaction time 90 minutes. When the solution of the product was processed by distilling, 39.4 g of tetra-n-butyl thiuram disulfide were obtained in the form of a yellowish oil, a yield corresponding to 96.6% of theoretical.

EXAMPLE 48

In the manner set forth in Example 1, tetra-i-butyl-thiuram disulfide was prepared from 25.8 g (0.2 mol) of di-i-butylamine, 16.0 g (0.21 mol) of carbon disulfide, and 20.2 g (0.2 mol) of triethylamine in the presence of 24.4 mg ($0.1 \times 10^{-3}$ mol) Mn(CH$_3$COO)$_2$·4H$_2$O and 100 g of isopropanol. The reaction temperature was 50° C., the oxygen pressure 1.8 bar, and the time of reaction 60 minutes. The white precipitate formed during cooling and concentrating of the reaction solution (FP=71° C.) consisted of 39.5 g of the desired thiuram disulfide, corresponding to 96.8% of theoretical.

EXAMPLE 49

In order to prepare ditetramethylene thiuram disulfide, 14.2 g (0.2 mol) of pyrrolidine, 16.0 g (0.21 mol) of carbon disulfide, 20.2 g (0.2 mol) of triethylamine, and 24.4 mg ($0.1 \times 10^{-3}$ mol) of Mn(CH$_3$COO)$_2$·4H$_2$O in 100 g of isopropanol were reacted with oxygen in the manner described in Example 1. The reaction temperature was 50° C., the oxygen pressure 1.8 bar and the time of reaction 45 minutes. The desired thiuram disulfide was deposited during the reaction as a white precipitate having a freezing point of 140° C., and was isolated in pure form. The yield was 27.8 g, corresponding to 95.2% of theoretical.

EXAMPLE 50

To prepare dipentamethylene thiuram disulfide, 17.0 g (0.2 mol) of piperidine, 16.0 g (0.21 mol) of carbon disulfide, 20.2 g (0.2 mol) of triethylamine and 24.4 mg ($0.1 \times 10^{-3}$ mol) of $Mn(CH_3COO)_2 \cdot 4H_2O$ in 100 g of isopropanol were reacted with oxygen in the manner described in Example 1. The reaction temperature was 50° C., the oxygen pressure 1.8 bar, and the reaction time required for a complete conversion was 85 minutes. The white precipitate (FP=132° C.) formed during the reaction consisted of the desired product, which was identified by physical and chemical analysis. The yield was 31.4 g, corresponding to 98.1% of theoretical.

EXAMPLE 51

In order to prepare N,N'-dimethyl-N,N'-dicyclohexyl thiuram disulfide, 22.6 g (0.2 mol) of N-methylcyclohexylamine, 16.0 g (0.21 mol) of carbon disulfide and 20.2 g (0.2 mol) of triethylamine in 100 g of isopropanol were reacted in the manner described in Example 1, in the presence of 24.4 mg ($0.1 \times 10^{-3}$ mol) of $Mn(CH_3COO)_2 \cdot 4H_2O$. The oxygen pressure was 1.8 bar, the reaction temperature 50° C. and the time of reaction until complete conversion was 95 minutes. The white precipitate formed during the reaction (FP=112° C.) was filtered off, washed, and dried, and was determined upon physical and chemical analysis to be 28.3 g of pure N,N'-dimethyl-N,N'-dicyclohexyl thiuram disulfide by chemical and physical analysis. The mother liquor contained another 7.4 g of this substance, which was separated by concentrating and washing the residue with alcohol. The yield was 35.7 g, corresponding to 94.9% of theoretical.

EXAMPLE 52

In order to prepare tetrabenzyl thiuram disulfide, 39.5 g (0.2 mol) of dibenzylamine, 10.1 g (0.1 mol) of triethylamine, and 16.0 g (0.21 mol) of carbon disulfide in 100 g of methanol were reacted in the manner described in Example 1, in the presence of 24.4 mg ($0.1 \times 10^{-3}$ mol) of $Mn(CH_3COO)_2 \cdot 4H_2O$. The oxygen pressure was 1.8 bar, the reaction temperature 50° C., and the time of reaction 3.5 hours. The white precipitate (FP=136° C.) formed during the reaction consisted of the desired thiuram disulfide, as determined by physical and chemical analysis. The yield was 52.5 g, which was 96.4% of theoretical.

What is claimed is:

1. A process for the preparation of thiuram disulfides substituted with aliphatic, araliphatic, or aromatic hydrocarbon radicals, said process comprising reacting a suitably substituted secondary amine with carbon disulfide in a solvent in the presence of a tertiary amine or ammonia, oxygen or an oxygen-containing gas, and metalliferous catalyst, wherein said carbon disulfide and said secondary amine are reacted in a molar ratio of 1.0 to 1.2:1, said reaction being maintained at a temperature between 0° and 200° C., said metalliferous catalyst being selected from the group consisting of elemental copper, copper(I) chloride, copper(I) bromide, copper(I) iodide, addition compounds of copper(I) halides with carbon monoxide, alkali chlorocuprates, complex ammoniacates of copper(I) cyanide, potassium tricyanocuprate(I), double salts with copper(I) thiocyanate, copper(I) acetate, copper(I) sulfide, complex double sulfides of copper(I) sulfide, alkali polysulfides, copper(II) chloride, copper(III) bromide, copper(II) sulfide, copper(II) nitrate, copper(II) thiocyanate, copper(II) cyanide, copper(II) acetate, copper dithiocarbamate, complex ammoniacates of copper(II) salts, copper(I) oxide, metallic cerium, cerium dioxide, cerium(III) chloride, cerium chloride, cerium chlorocomplex salts, cerium nitrate, cerium nitrato salts, cerium sulfate, cerium carbonate, cerium oxalate, cerium sulfides, vanadium oxide, vanadium chloride, vanadium sulfates, molybdenum oxides, molybdenum chloride, molybdenum sulfide, molybdenum fluoride, molybdates, molybdenum complex acido salts, powdered manganese, manganese dioxide, potassium permanganates, manganese dithiocarbamates, manganese acetate, the manganese derivatives corresponding to the above copper compounds, iron oxides, iron(II) and iron(III) salts, complex iron salts, cobalt oxides, cobalt(II) salts, cobalt complex salts, and double and complex vanadium salts.

2. The process as set forth in claim 1, wherein from 0.01 to 5 millimoles of said metalliferous catalyst is used per mole of secondary amine.

3. The process as set forth in claim 1 or 2, wherein said solvent is selected from one or more of the group including an aromatic hydrocarbon, a $C_1$–$C_4$ alcohol, and water.

4. A process for the preparation of thiuram disulfides substituted with aliphatic, cycloaliphatic, araliphatic and or aromatic hydrocarbon radicals, said process comprising reacting carbon disulfide, a suitably substituted secondary amine, and a tertiary amine or ammonia in equimolar quantities to form a mixture, and reacting said mixture with carbon disulfide in the presence of oxygen or a gas containing oxygen, a solvent, and a metalliferous catalyst, said reaction being maintained at a temperature between 0° C. and 200° C., said metalliferous catalyst being selected from the group consisting of elemental copper, copper(I) chloride, copper(I) bromide, copper(I) iodide, addition compounds of copper(I) halides with carbon monoxide, alkali chlorocuprates, addition compounds of copper(I) halides with carbon monoxide, alkali chlorocuprates, complex ammoniacates of copper(I) cyanide, potassium tricyanocuprate(I), double salts with copper(I) thiocyanate, copper(I) acetate, copper(I) sulfide, complex double sulfides of copper(I) sulfide, alkali polysulfides, copper(II) chloride, copper(II) bromide, copper(II) sulfide, copper(II) nitrite, copper(II) thiocyanate, copper(II) cyanide, copper(II) acetate, copper dithiocarbamate, complex ammoniacates of copper(II) salts, copper(I) oxide, metallic cerium, cerium dioxide, cerium(III) chloride, cerium chloride, cerium chlorocomplex salts, cerium nitrate, cerium nitrato salts, cerium sulfate, cerium carbonate, cerium oxalate, cerium sulfides, vanadium oxide, vanadium chloride, vanadium sulfates, molybdenum oxides, molybdenum chloride, molybdenum sulfide and molybdenum fluoride, molybdates, molybdenum complex acido salts, powered manganese, manganese dioxide, potassium permanganates, manganese dithiocarbamates, manganese acetate, the manganese derivatives corresponding to the above copper compounds, iron oxides, iron(II) and iron(III) salts, complex iron salts, cobalt oxides, cobalt(II) salts, cobalt complex salts, and double and complex vanadium salts.

5. The process as set forth in claim 4, wherein from 0.01 to 5 millimoles of said metalliferous catalyst is used per mole of secondary amine.

6. The process as set forth in claim 4 or 5, wherein said solvent is selected from one or more of the group including an aromatic hydrocarbon, a $C_1$–$C_4$ alcohol, and water.

7. A process for the preparation of thiuram disulfides substituted with aliphatic, cycloaliphatic, araliphatic, or aromatic hydrocarbon radicals, said process comprising reacting carbon disulfide, a suitably substituted secondary amine and a tertiary amine or ammonia to form a dithiocarbamate, and reacting said dithiocarbamate in the presence of a metalliferous catalyst, a solvent, and oxygen or an oxygen-containing gas, said process being maintained at a reaction temperature between 0° C. and 200° C., said metalliferous catalyst being selected from the group consisting of elemental copper, copper(I) chloride, copper(I) bromide, copper(I) iodide, addition compounds of copper(I) halides with carbon monoxide, alkali chlorocuprates, complex ammoniacates of copper(I) cyanide, potassium tricyanocuprate(I), double salts with copper(I) thiocyanate, copper(I) acetate, copper(I) sulfide, complex double sulfides of copper(I) sulfide, alkali polysulfides, copper(II) chloride, copper(II) bromide, copper(II) sulfide, copper(II) nitrite, copper(II) thiocyanate, copper(II) cyanide, copper(II) acetate, copper dithiocarbamate, complex ammoniacates of copper(II) salts, copper(I) oxide, metallic cerium, cerium dioxide, cerium(III) chloride, cerium chloride, cerium chlorocomplex salts, cerium nitrate, cerium nitrato salts, cerium sulfate, cerium carbonate, cerium oxalate, cerium sulfides, vanadium oxide, vanadium chloride, vanadium sulfates, molybdenum oxides, molybdenum chloride, molybdenum sulfide, molybdenum fluoride, molybdates, molybdenum complex acido salts, powdered managnese, manganese dioxide, potassium permanganates, manganese dithiocarbamates, manganese acetate, the manganese derivatives corresponding to the above copper compounds, iron oxides, iron(II) and iron(III) salts, complex iron salts, cobalt oxides, cobalt(II) salts, cobalt complex salts, and double and complex vanadium salts.

8. The process as set forth in claim 7, wherein from 0.01 to 5 millimoles of said metalliferous catalyst is used per mole of dithiocarbamate.

9. The process as set forth in claim 7 or 8, wherein said solvent is selected from one or more of the group including an aromatic hydrocarbon, a $C_1$–$C_4$ alcohol, and water.

* * * * *